(12) United States Patent
Bossler

(10) Patent No.: US 9,364,295 B2
(45) Date of Patent: Jun. 14, 2016

(54) CLAMPING DEVICE FOR A DENTAL TOOL IN A DENTAL TURBINE HANDPIECE

(75) Inventor: Juergen Bossler, Leutkirch (DE)

(73) Assignee: Minebea Co., Ltd., Nagano (JP)

( * ) Notice: Subject to any disclaimer, the term of this patent is extended or adjusted under 35 U.S.C. 154(b) by 156 days.

(21) Appl. No.: 13/240,644

(22) Filed: Sep. 22, 2011

(65) Prior Publication Data

US 2012/0244495 A1 Sep. 27, 2012

(30) Foreign Application Priority Data

Sep. 27, 2010 (DE) .......................... 10 2010 037791

(51) Int. Cl.
*A61C 1/14* (2006.01)
*B23B 31/14* (2006.01)

(52) U.S. Cl.
CPC ................ *A61C 1/141* (2013.01); *A61C 1/142* (2013.01); *B23B 31/14* (2013.01); *Y10T 279/247* (2015.01)

(58) Field of Classification Search
CPC ...... B23B 31/14; Y10T 279/247; A61C 1/14; A61C 1/141; A61C 1/144; A61C 1/05
USPC .......................... 433/114, 126, 127, 128, 129
See application file for complete search history.

(56) References Cited

U.S. PATENT DOCUMENTS

| 5,634,933 | A | 6/1997 | McCombs et al. |
| 2007/0184407 | A1* | 8/2007 | Duesing ........................ 433/129 |
| 2007/0243499 | A1 | 10/2007 | Bowen |

FOREIGN PATENT DOCUMENTS

GB 1118828 7/1968

OTHER PUBLICATIONS

Foreign Search Report.

* cited by examiner

*Primary Examiner* — Heidi M Eide
(74) *Attorney, Agent, or Firm* — Duane Morris LLP

(57) ABSTRACT

A clamping device for a dental tool in a dental turbine handpiece having at least one clamping lever that is supported in a fulcrum and that extends along the axis of a tool shank to be clamped, wherein the clamping lever is designed and arranged such that the tool shank can be clamped using the clamping lever and that on rotation of the clamping device, through the effect of the centrifugal force, the clamping lever is radially deflected about the virtual fulcrum, so as to increase the clamping force acting on the tool shank.

12 Claims, 10 Drawing Sheets

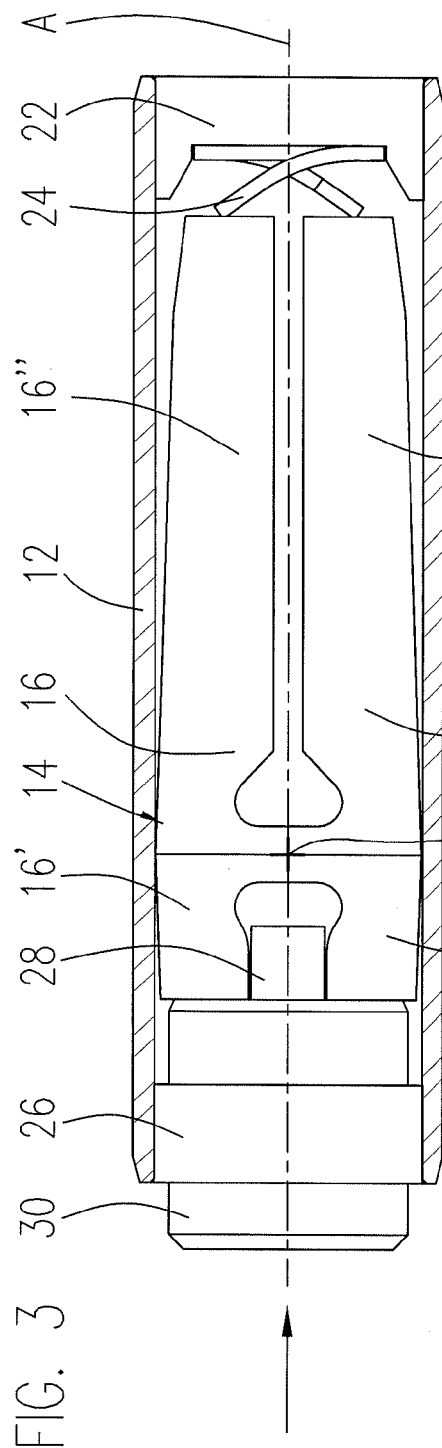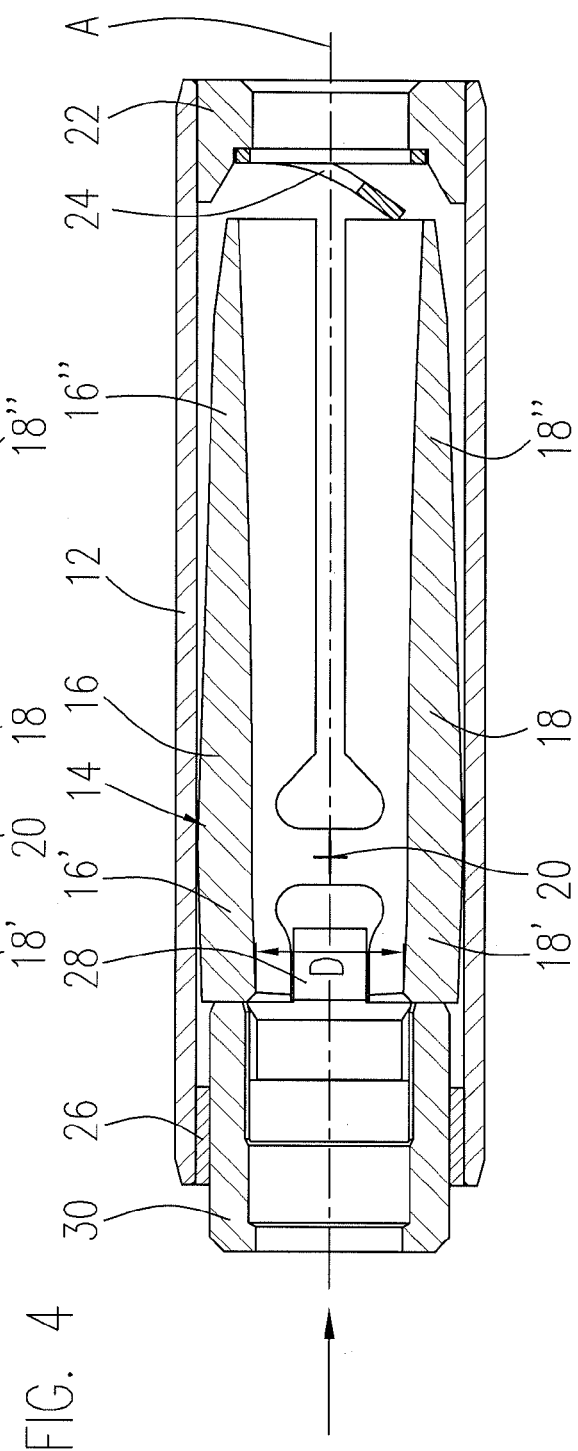

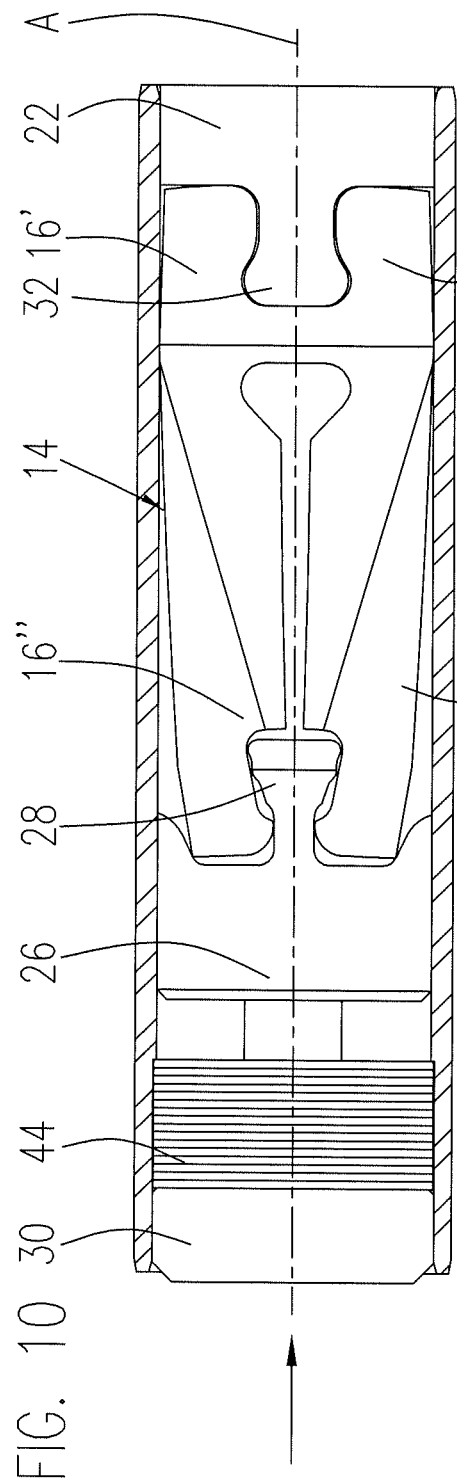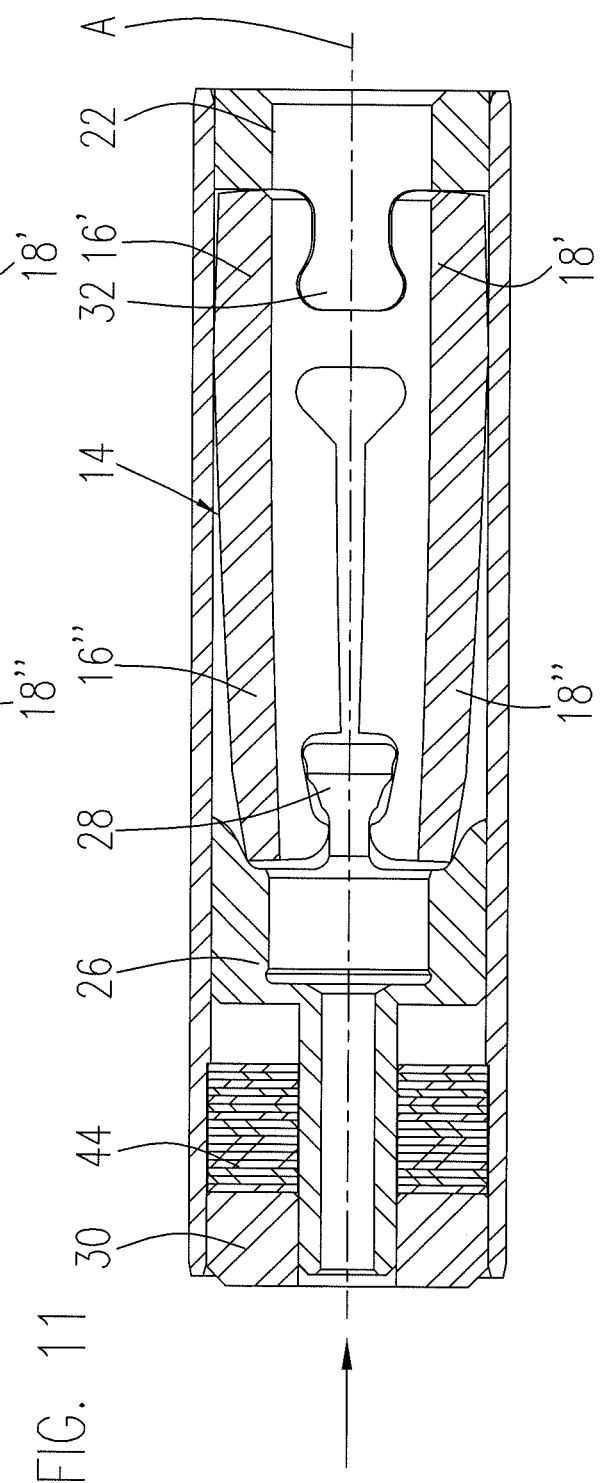

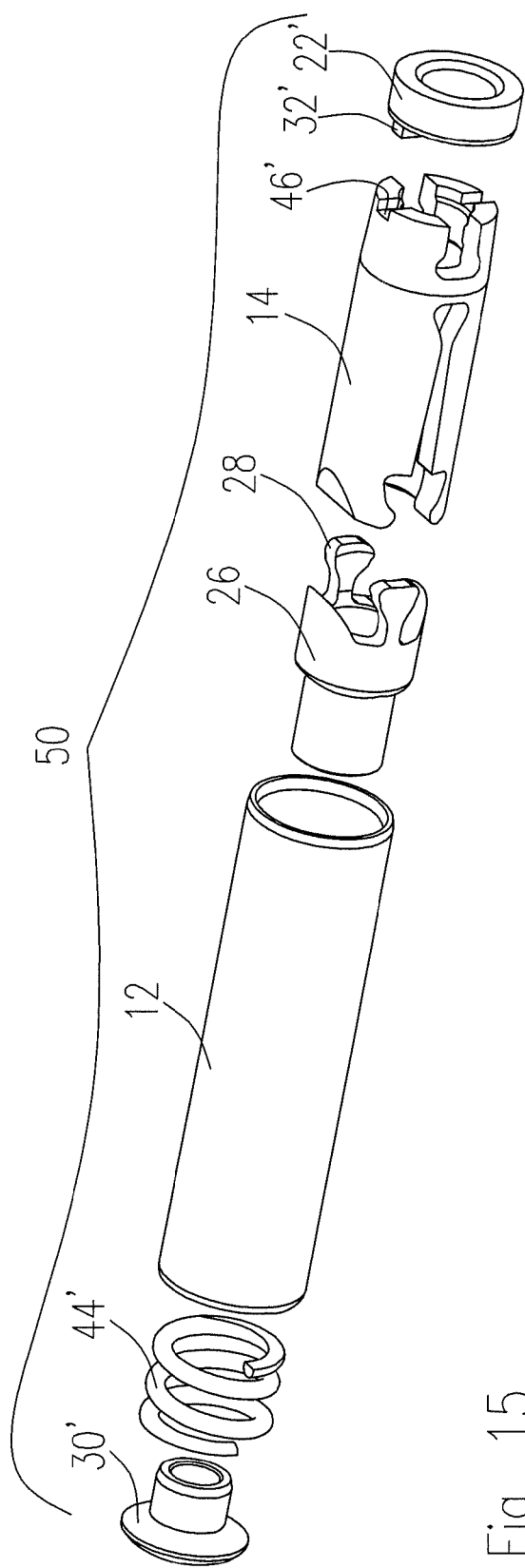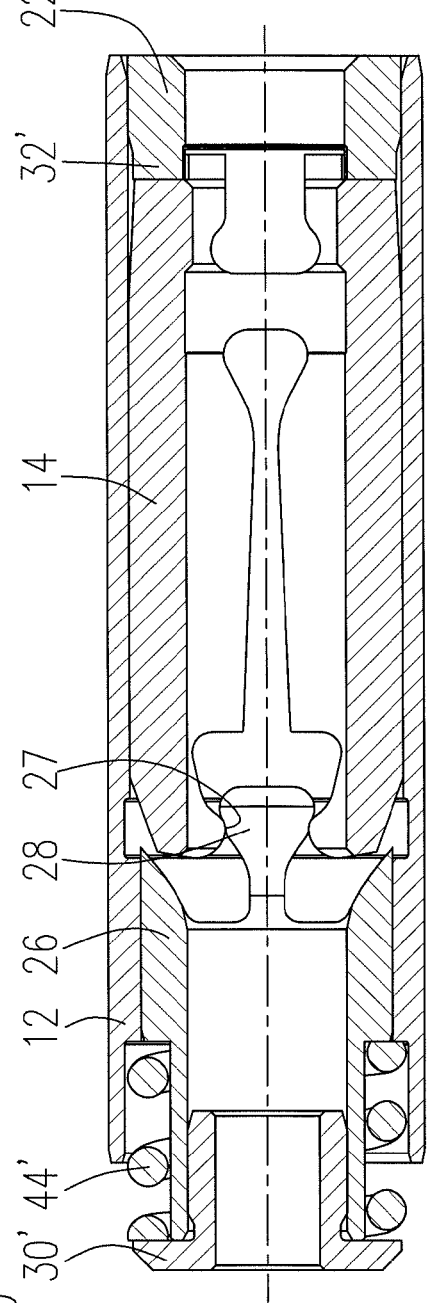

CLAMPING DEVICE FOR A DENTAL TOOL IN A DENTAL TURBINE HANDPIECE

RELATED APPLICATION

Figure 1:
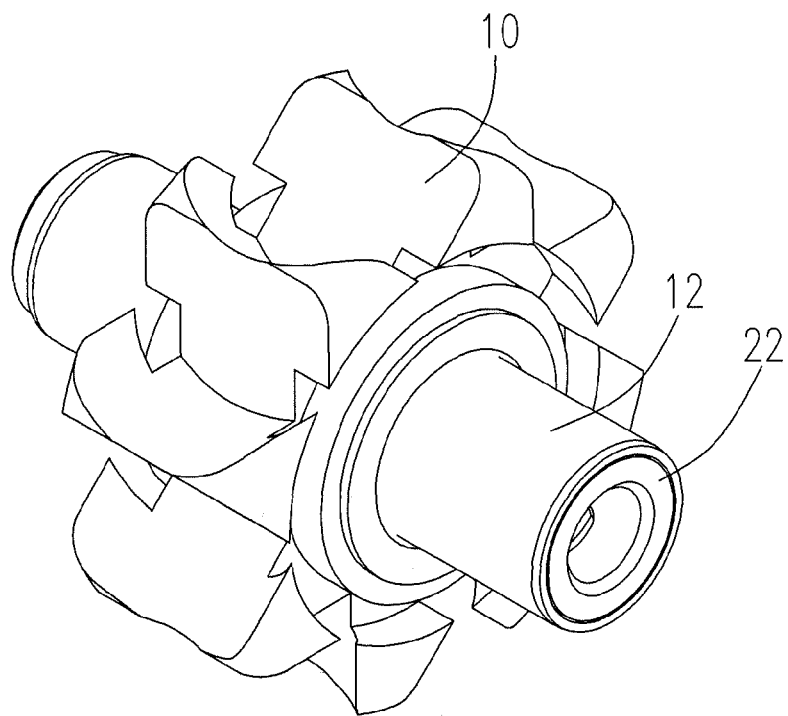

The instant application claims the priority benefit of German Patent Application No. 102010037791.0 filed on 27 Sep. 2010, the entirety of which is hereby incorporated herein by reference.

FIELD OF INVENTION

The invention relates to a clamping device for a dental tool in a dental turbine handpiece, used particularly for high-speed air turbines that operate at high rotational speeds of about 200,000 to 500,000 rpm.

BACKGROUND OF THE INVENTION

Dental handpieces operated by air turbines have a turbine rotor that is supported in a housing a sliding bearing or a ball bearing. The turbine rotor has turbine blades at its circumference as well as a clamping device for clamping the shank of a dental tool within a housing, the turbine blades being mounted on the outside surface of this housing. In order to fit and change the tool, push-button clamping systems are known that do not require an extra tool for a tool change. Two popular designs for push-button clamping systems have gained acceptance. In one design, a taper is used in conjunction with a pressure spring. The other design is based on the elastic deformation of a specially constructed component that is shown, for example, in EP 1 232 731 B1.

A known clamping device that is described in CH 631 068 A has a chuck having a plurality of tensioning claws and a clamping piece that interacts with the tensioning claws. The clamping piece clamps the tensioning claws from the outside towards the inside in the direction of the tool shank, so that the tensioning claws concentrically exert a clamping force on the tool shank. The shank of the dental tool is thereby securely clamped. However, the difficulty arising here is that when the turbine rotor is at a standstill, the shank of the dental tool continues to be securely held in the clamping device, whereas the holding force during operation decreases due to the centrifugal forces acting on the tensioning claws. Moreover, in this design it is necessary to operate the clamping device manually when fitting and releasing the dental tool.

CH 631 068 A further describes that likewise when fitting and removing a dental tool by means of elastic clamping using a plastic or rubber element, there is the difficulty that centrifugal forces act on the elastic clamping device and again during operation the holding force thus decreases in a centripetal direction.

CH 631 068 A therefore proposes an air turbine handpiece having a clamping piece within the turbine rotor body in which the chuck is fitted and arranged so as to be slideable in an axial direction. On its front part, the chuck has a large number of tensioning claws, and on its opposed rear end there is located a flange which supports an elastic ring. When the turbine rotor body rotates, the centrifugal force spreads the ring apart and thus presses it against the tensioning sleeve which is advanced in the clamping piece. The tensioning claws are thereby clamped together convergently, so that the shank of the dental tool remains securely clamped even at increasing rotational speeds.

US 2002/0105149 A1 also deals with the problem of a decreasing clamping force as the rotational speed of the dental turbine increases, due to the increasing centrifugal force. This document proposes a solution for a clamping device of a dental tool having a housing in which a drill sleeve is inserted. The aim of the design is to allow easy insertion of a dental drill when the dental turbine is at a standstill and to lock it in place using the centrifugal forces that act during rotation. For this purpose, locking weights are provided within the housing that are supported at associated fulcrums and, on rotation of the dental turbine, pivot in a radial direction about their fulcrums and come to rest against the shank of the dental drill in order to lock it in position. The weights pivoting in a radial direction jut out and can only be disposed near the turbine head. It is not possible to accommodate them within the inside diameter of the turbine blade to save space.

The systems described achieve a certain improvement with regard to the problems caused by centrifugal forces occurring on rotation. In practice, however, the solutions have not proved very useful.

The basic requirement placed on a clamping device for a dental tool in a dental turbine handpiece is that it should be possible to change the dental tool with the least possible actuating force and without the need for extra tools. This actuating force, however, must not be made so small that unintended triggering, such as by touching the cheek of a patient, is made possible. The holding force must be sufficient to lock in the dental tool reliably and securely under all operating conditions. A desirable clamping system is thus one that is simple and fast to operate and that has sufficient holding force to clamp a dental tool reliably. Since nowadays a cylindrical shank is always standard for dental tools, it is not possible to have form-locking clamping of the shank of the dental tool in order to secure the dental tool against axial displacement and against rotation. Rather, it is necessary to hold the dental tool in position using a frictional connection and the resulting frictional forces. Here, the clamping device has to be designed such that, even for centrifugal forces acting at very high rotational speeds from up to 450,000 rpm and more, it holds the dental tool reliably, since even dental handpieces having ball bearings nowadays reach rotational speeds of up to 450,000 rpm. A solution is sought that makes use of these centrifugal forces for clamping the dental tool in a simple manner so that on rotation of the dental turbine, the holding force definitely does not decrease in relation to a stationary system.

SUMMARY OF THE INVENTION

The invention proposes a clamping device for a dental tool in a dental turbine handpiece, said clamping device having at least one clamping lever that can be deflected about a virtual fulcrum or about a virtual rotational axis and that extends along the axis of the tool shank to be clamped. The clamping lever is designed and disposed such that it clamps the tool shank, wherein, through the effect of the centrifugal force during rotation of the clamping device, the clamping lever is deflected about the virtual fulcrum or the virtual rotational axis and thereby increases the clamping force acting on the tool shank. The virtual rotational axis of the clamping lever preferably extends perpendicular to the axis of the tool shank to be clamped.

The clamping lever is preferably designed as a two-armed clamping lever having a first and a second lever arm deflectable about the virtual fulcrum. The tool is clamped by the first lever arm, wherein, through the effect of the centrifugal force during rotation of the clamping device, the second lever arm is deflected about the virtual fulcrum and thus increases the clamping force of the first lever arm. It is particularly preferable if the clamping lever forms a part of a collet that has a plurality of clamping levers preferably disposed evenly about the axis of the tool shank to be clamped. In a preferred embodiment of the invention, the collet has two opposing clamping levers. The clamping device according to the invention may, however, be realized with only one clamping lever or with three or more clamping levers.

The clamping device according to the invention is designed such that due to the high rotational speed, high centrifugal forces act on the clamping lever, these centrifugal forces being used to increase the clamping force acting on the tool. The rotational speed of the dental turbine is thereby utilized in order to achieve a specific holding force that increases as the rotational speed increases.

In the preferred embodiment, a two-armed clamping lever is used in which the mass of the second lever arm is greater than the mass of the first lever arm, so that through the effect of centrifugal forces, the clamping lever is deflected in the region of the second lever arm and thereby presses the first lever arm against the shank of the dental tool. Since the clamping lever extends along the axis of the tool shank to be clamped, the axial length of the dental turbine handpiece, in extension of the axis of the dental tool, can be used to accommodate a relatively long clamping lever with the appropriate distribution of mass. By contrast, the weights in US 2002/0105149 A1 extend, for example, outside the tool shank and are deflected at an axis parallel to it. What is more, less space is required by the clamping device according to the invention. It can be accommodated in a cylindrical housing that passes through the impeller of the dental turbine. The outside diameter of the clamping device is thus no larger than the inside diameter of the impeller.

In the preferred embodiment, the collet is supported in a housing so as to be displaceable in an axial direction. A guide bushing is also accommodated in this housing, the collet being inserted in an axial direction into the guide bushing. The guide bushing is designed such that it presses the second, longer lever arm of the clamping lever in the direction of the axis of the tool to be clamped when it is pushed into the guide bushing. The first, shorter lever aim thereby moves away from the axis of the tool to be clamped, allowing the tool to be more easily loosened.

For this purpose, the guide bushing is preferably fixed in the housing and has a wedge-shaped inner surface along which the second lever arm of the clamping lever slides, so that on entry into the bushing, it is pressed in the direction of the axis of the tool shank to be clamped and on emerging out of the bushing it can move away from the axis of the tool shank.

In a further embodiment of the invention, which can be combined with the above-mentioned features, the clamping device has a locking device by means of which the clamping lever can be releasably locked in an axial direction. For this purpose, for example, a detent mechanism is used that locks the clamping lever in a predetermined position with respect to the housing. The detent mechanism may, for example, have a ball which is moveable between the housing and the clamping lever in a radial direction.

In an advantageous embodiment of the invention, which can be combined with the above-mentioned features, a push-button mechanism is provided that acts in an axial direction on the collet so as to displace the latter in an axial direction. The clamping lever may thereby be pressed, for example, into the guide bushing in order to press the second lever aim in the direction of the axis of the tool to be clamped and thus to reduce the clamping force of the first lever arm when a tool change needs to be carried out. On releasing the push-button, the clamping lever slides out of the guide bushing and, due to centrifugal forces during rotation of the clamping device, the second lever arm is pressed away from the axis of the tool to be clamped. The axial displacement of the clamping lever out of the guide bushing can be supported by a return mechanism or, with an appropriate guide bushing design, also can be caused by the influence of the centrifugal force.

In a further advantageous embodiment of the invention, a spreading element or engaging piece is provided in the region of the second lever arm, for example, on the guide bushing, against which the clamping lever comes to rest when it slides out of the guide bushing. The spreading element exerts a force acting outwards in a radial direction or in the direction of the circumference on the second lever arm, so as to spread it away from the axis of the tool shank to be clamped and thus to maintain the clamping force of the first lever arm. The spreading element is preferably connected to the housing in a torque-proof manner, and additionally forms an engaging piece for the clamping lever. When two or more clamping levers form a collet, the spreading element is preferably inserted between the second (longer) lever arms of adjoining clamping levers in order to press them apart. Due to inertia at the beginning of the movement, the transport of the second lever arm by the spreading element, causes contortion and thus additional spreading of these lever arms and consequently an intensification of the deflection of the clamping lever away from the axis of the tool shank to be clamped.

The clamping lever is preferably elastically deformable.

SHORT DESCRIPTION OF DRAWINGS

Figure 2:
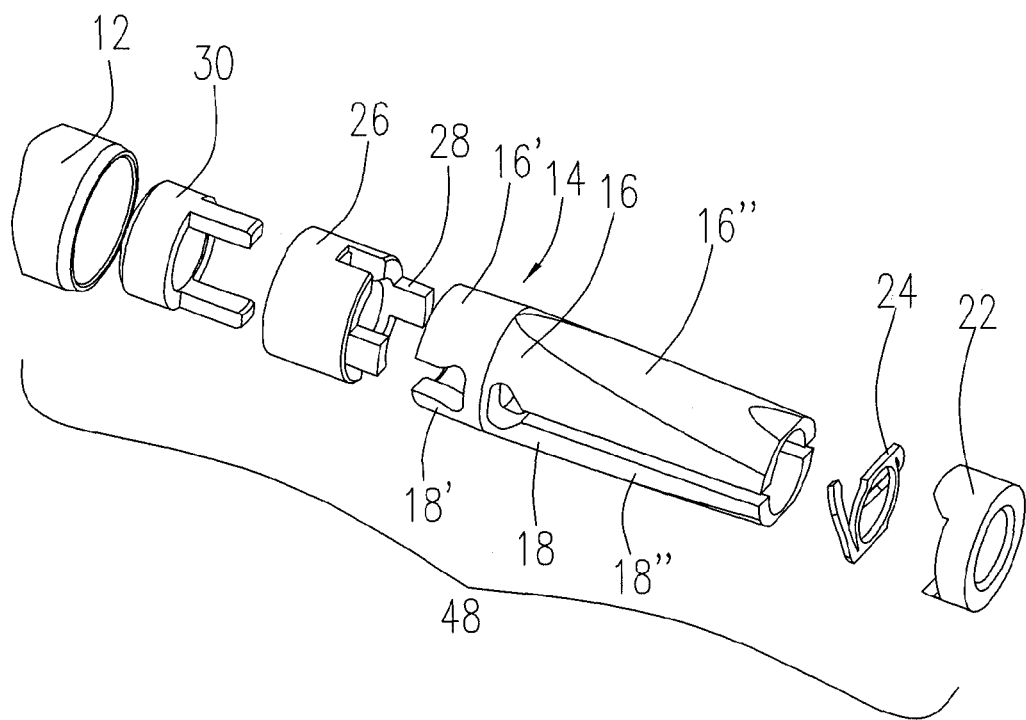
Figure 5:
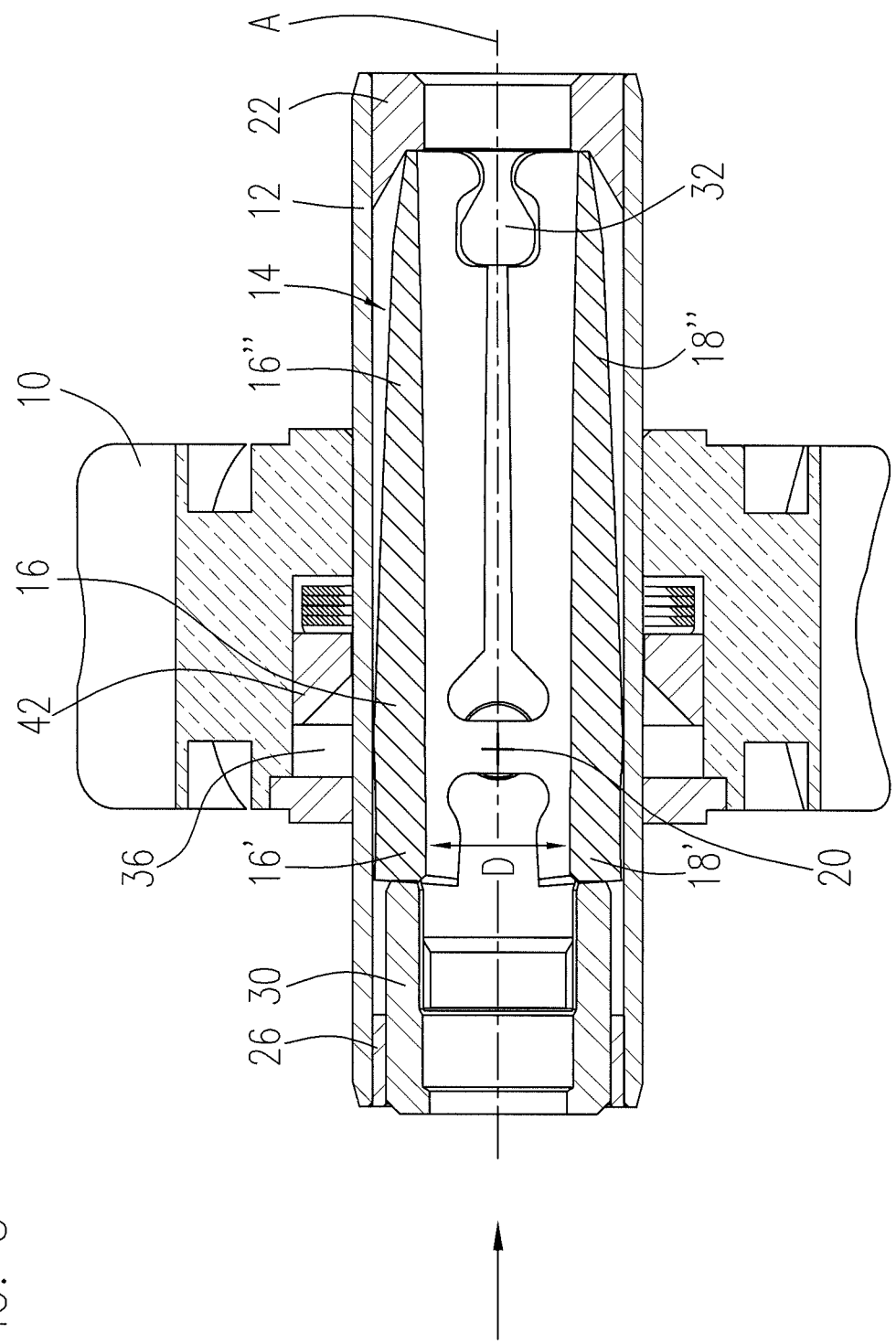
Figure 6:
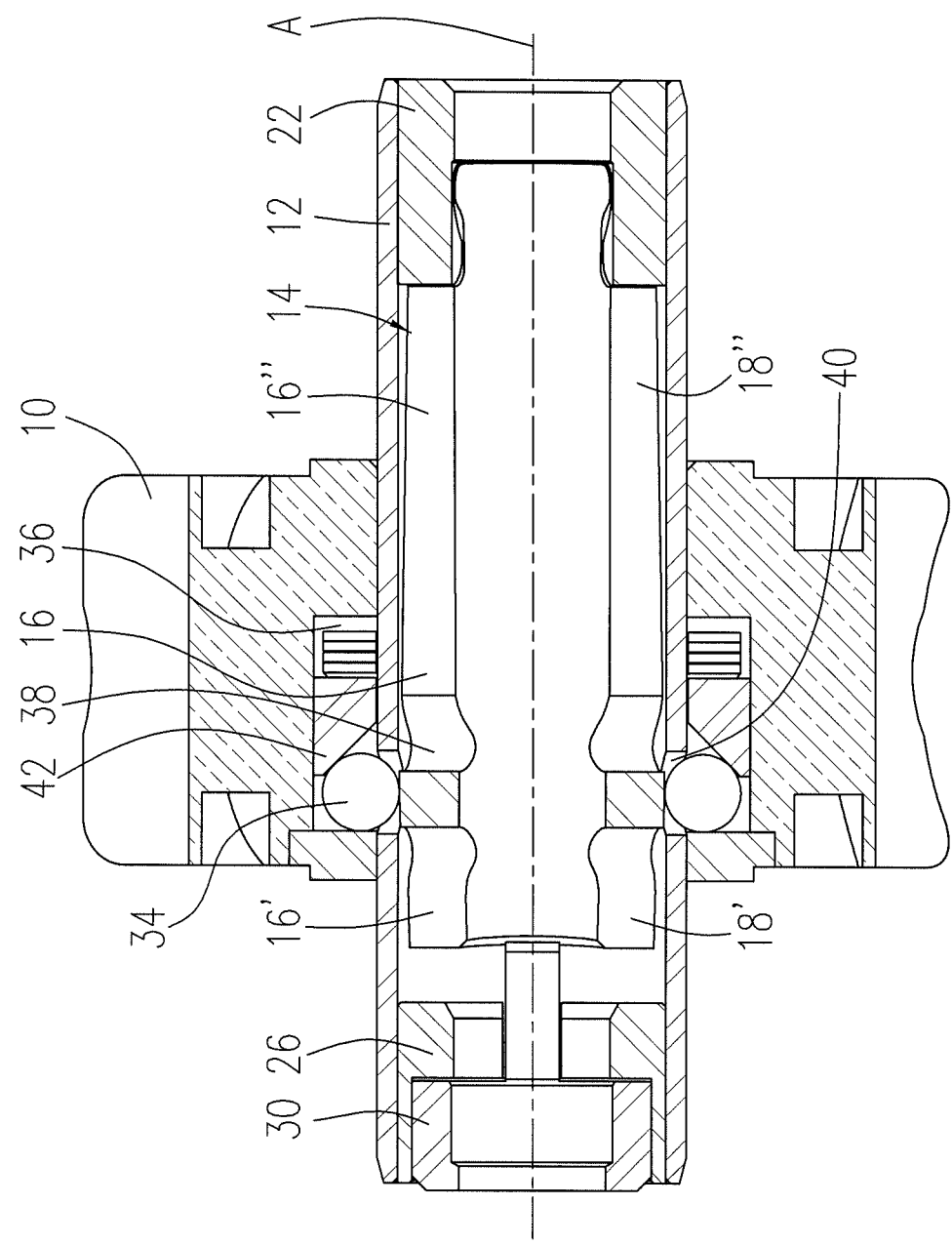
Figure 7:
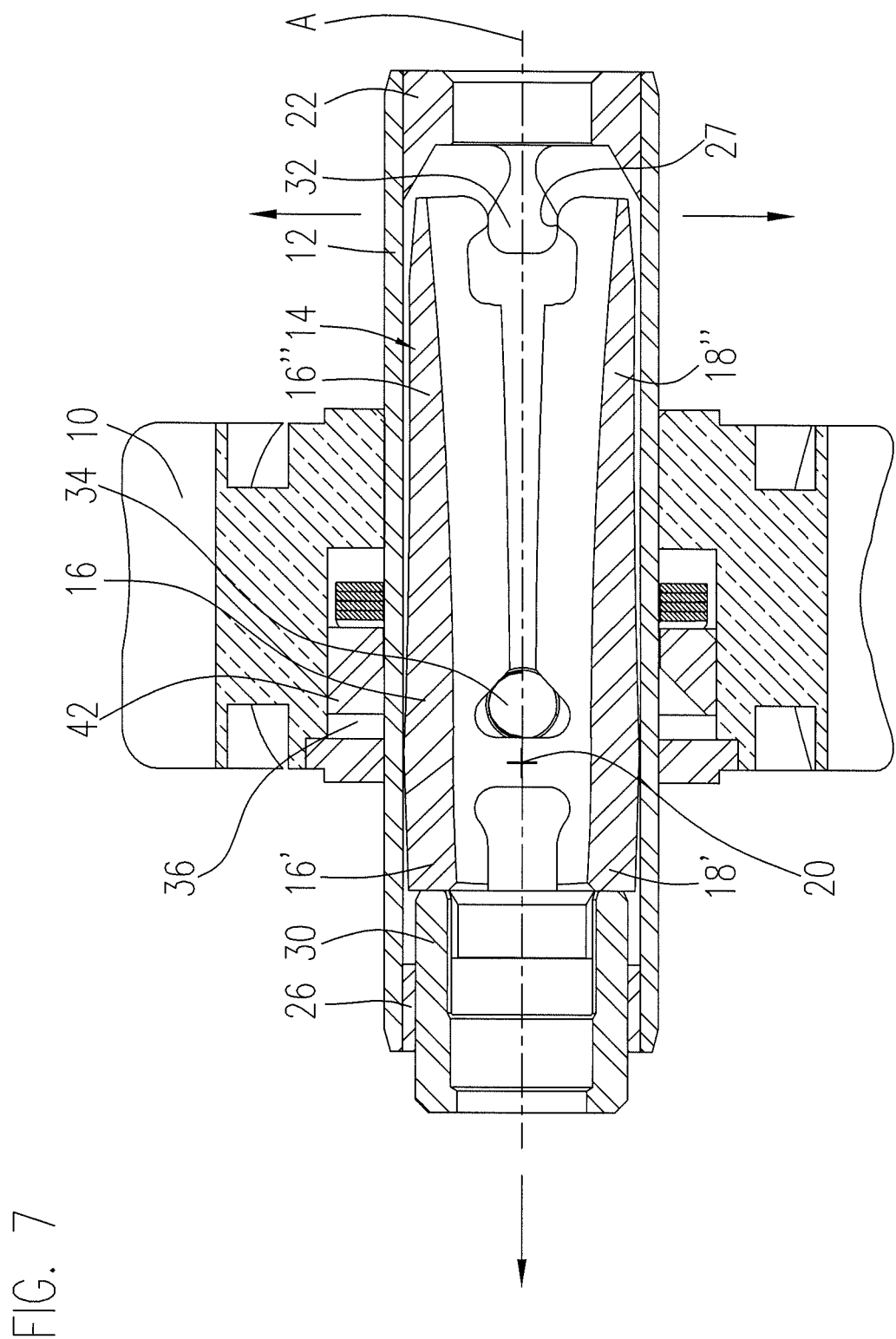
Figure 8:
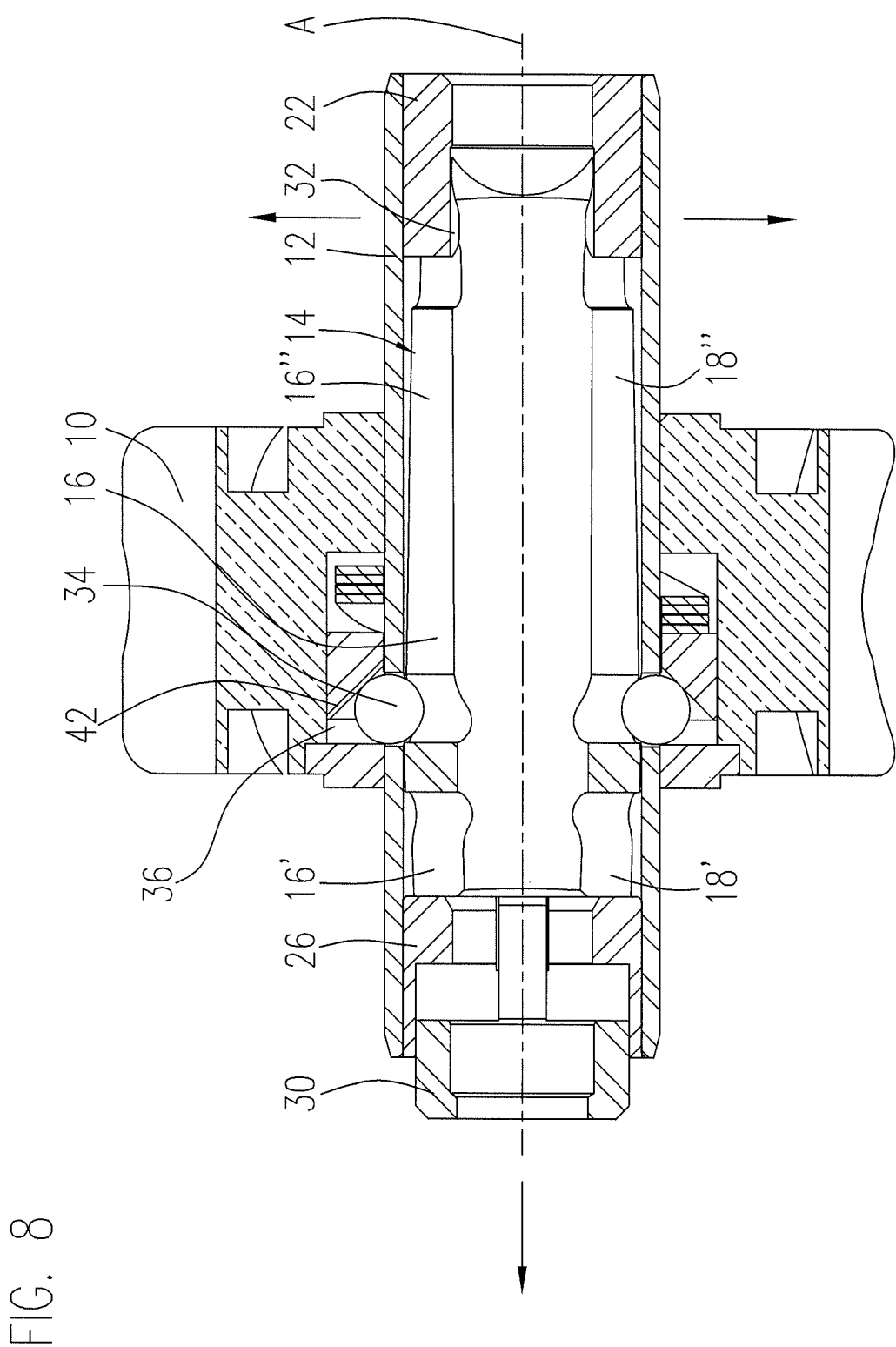
Figure 9:
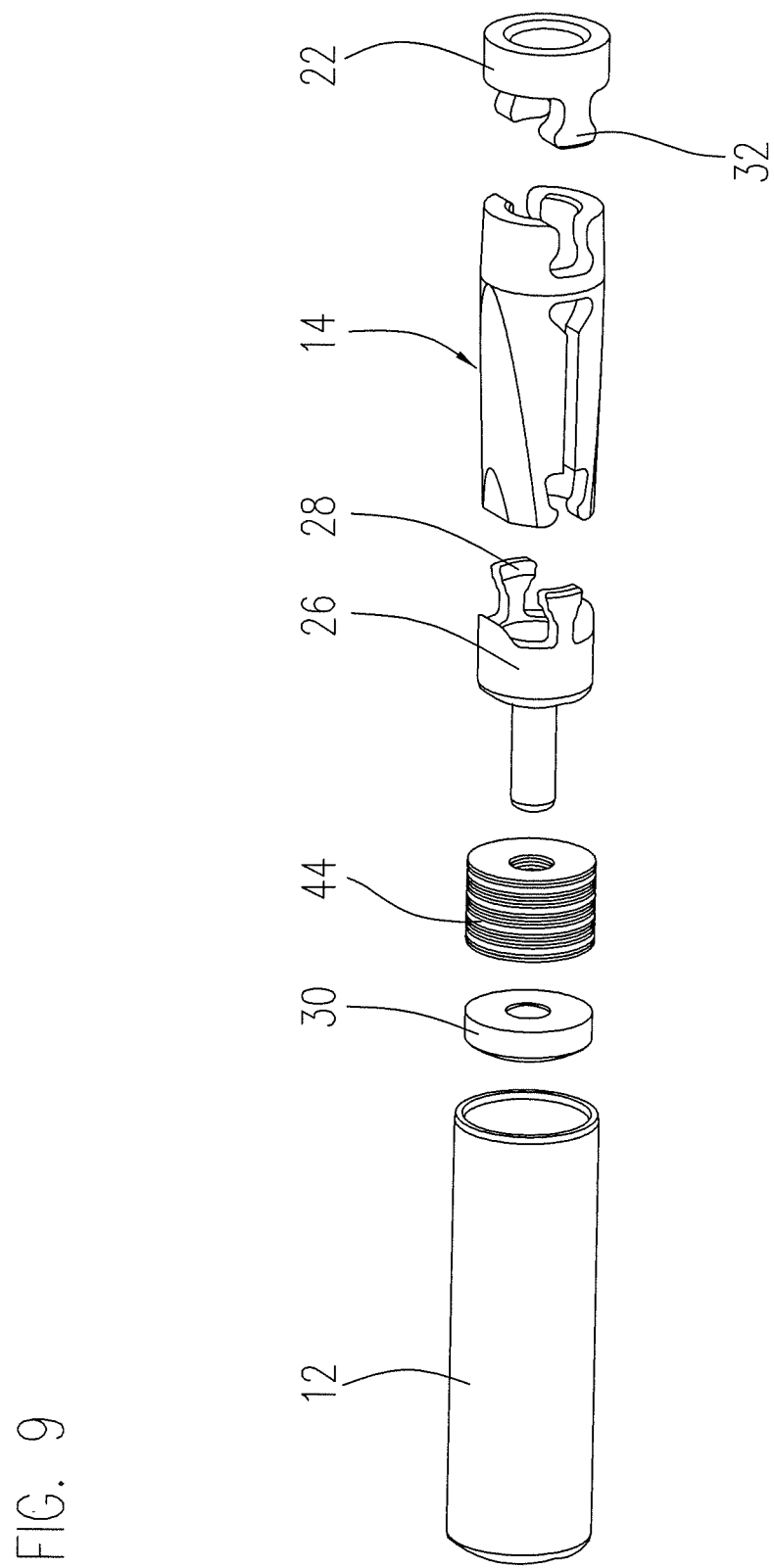
Figure 12:
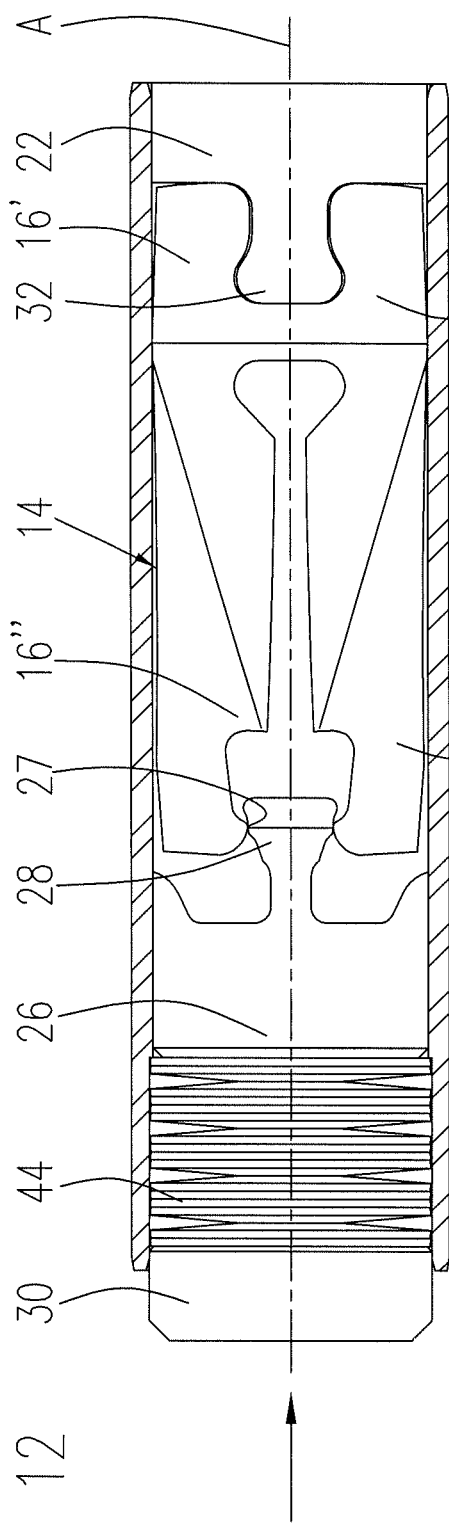
Figure 13:
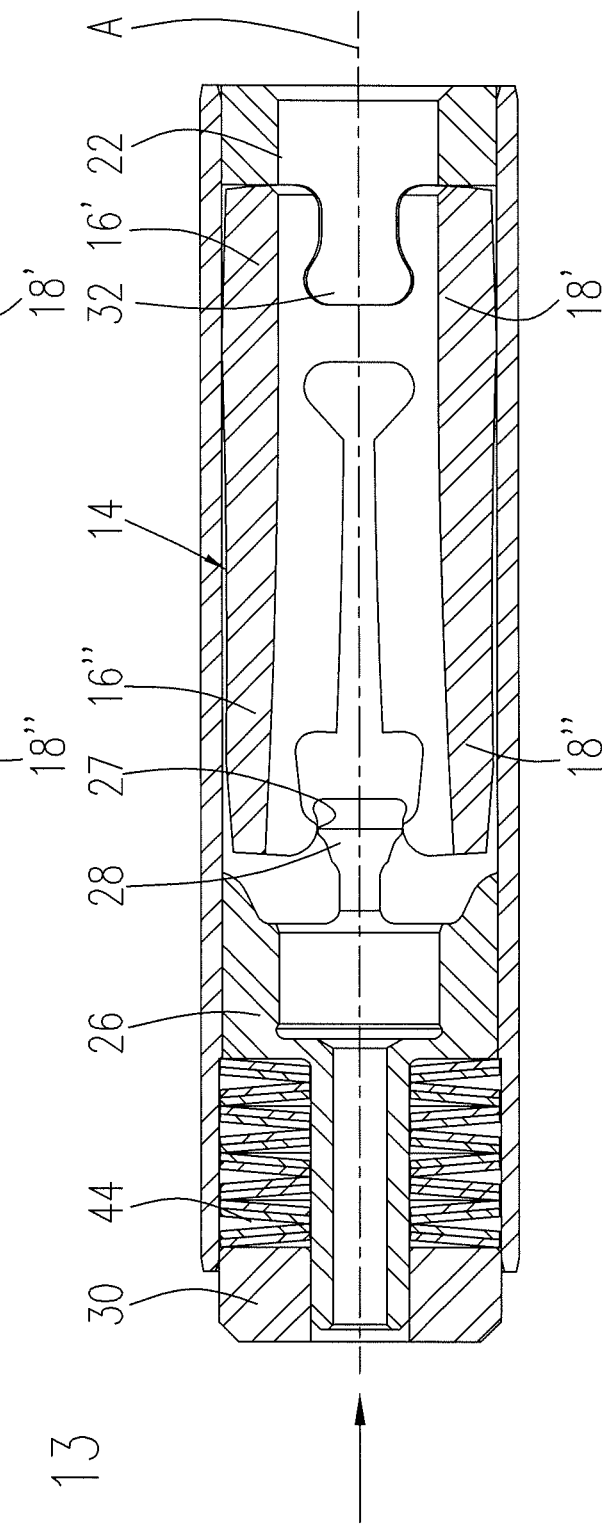

The invention is described in more detail below on the basis of preferred embodiments with reference to the drawings. The figures show:

FIG. 1 a perspective view of a dental turbine according to the invention;

FIG. 2 an exploded view of a clamping device according to a first embodiment for the dental turbine of FIG. 1;

FIG. 3 a partial section of the clamping device of FIG. 2 in an assembled state, in a stationary position;

FIG. 4 a sectional view through the clamping device of FIG. 3;

FIG. 5 a sectional view through the dental turbine of FIG. 1 having a clamping device according to a second embodiment, in a position for loosening the tool;

FIG. 6 a sectional view through the dental turbine of FIG. 5, but turned by 90° compared to the view of FIG. 5;

FIG. 7 a sectional view through the dental turbine of FIG. 5, wherein the clamping device is in a position for clamping the tool;

FIG. 8 a sectional view through the dental turbine of FIG. 7, but turned by 90° compared to the view of FIG. 7;

FIG. 9 an exploded view of a clamping device according to a further embodiment of the invention;

FIG. 10 a partial section of the clamping device of FIG. 9 in an assembled state, in a position for loosening the tool;

FIG. 11 a sectional view through the clamping device of FIG. 10;

FIG. 12 a partial section of the clamping device of FIG. 9 in an assembled state, in a position for clamping the tool;

FIG. 13 a sectional view through the clamping device of FIG. 12;

FIG. 14 an exploded view of a clamping device according to a modification on the previously described embodiments; and FIG. 15 a sectional view through the clamping device of FIG. 14, wherein the clamping device is shown in a position for clamping the tool.

DETAILED DESCRIPTION OF EMBODIMENT

FIG. 1 shows a perspective view of a dental turbine that includes a clamping device for a dental tool according to the invention. The turbine comprises an impeller 10 having turbine blades that is located on a housing 12 which encloses the clamping device. The housing 12 is preferably cylindrical or substantially cylindrical and fits into the inside diameter of the impeller 10. The housing 12 can be supported using ball bearings in a dental turbine handpiece (not illustrated). Dental turbines must naturally have small dimensions in order to be accommodated in a dental turbine handpiece. To achieve the necessary cutting performance, high rotational speeds have to be attained, for example, in the range of 200,000 to 500,000 rpm. Due to the small dimensions of the blades of the impeller, torque is limited. When subject to load, there is a noticeable drop in rotational speed compared to the no-load speed. Thus on rotation of the dental turbine, considerable centrifugal forces act on the clamping device, where the rotational speed and thus the centrifugal force as well drop when subject to load. The invention makes use of the centrifugal force created by rotation to increase the clamping force of the clamping device on the dental tool and, in addition, in one embodiment provides means that counteract the decreasing centrifugal force when the rotational speed drops.

A first embodiment of the invention is shown in FIGS. 2 to 4.

In a preferred embodiment of the invention, the clamping device 48 comprises a collet 14 having a first and a second clamping lever 16, 18. The clamping levers 16, 18 each comprise a first, shorter lever arm 16', 18' and a second, longer lever arm 16", 18". The clamping levers 16, 18 are deflectable about a virtual fulcrum or a virtual rotational axis 20 that is indicated in the figures by a cross. The virtual rotational axis 20 extends perpendicular to the axis A of the tool shank to be clamped and preferably intersects it. The clamping levers 16, 18 extend substantially parallel to the axis A of the tool shank to be clamped and can be accommodated in the housing 12 requiring minimum space. The second, longer lever arms 16", 18", also called wings, have the greatest possible length in order to achieve a large leverage effect with a small deflection. The clamping levers 16, 18 are preferably made of a metal, such as stainless steel, and are elastically deformable, pivoting of the second, longer lever arm 16", 18" being transmitted to the first, shorter lever arm 16', 18'. The shorter lever arms are thereby used to lock in or clamp a tool shank, and the longer lever arms are used as wings to intensify the clamping force.

The clamping device further comprises a first guide bushing 22, a return spring 24, a second guide bushing 26 having an engaging piece 28 and a push button 30. The clamping device is fixedly mounted against rotation and supported in the housing 12 via the stationary guide bushings 22, 26 and the engaging piece 28. The clamping device and the housing 12 rotate together with the turbine impeller 10.

The collet 14 together with the two clamping levers 16, 18 can be moved in the housing 12 in an axial direction by pressing the push button 30. When the push button 30 is pressed into the housing 12 (see arrow), the clamping levers 16, 18 of the collet 14 are pushed into the first guide bushing 22. The guide bushing 22 has a wedge-shaped inner surface, so that the two wings 16", 18" are pressed together when they enter into the first guide bushing 22. The clamping levers are thereby elastically deformed, so that the clamping diameter D between the two first, shorter lever arms 16', 18' widens. This clamping diameter D ultimately determines the frictional connection between the clamping device and the tool shank to be received (not illustrated). If it is widened, the tool may be easily inserted manually, from the right in the drawing.

Once the push button 30 is released, the collet 14 is pushed substantially or completely out of the first guide bushing 22 by means of the return spring 24, so that the wings 16", 18" of the clamping levers 16, 18 can be released. They return to their original position as shown in FIGS. 3 and 4 in which a dental tool would be firmly clamped in the region of the clamping diameter D.

When the dental turbine rotates in operation, the centrifugal forces thus created cause a leverage effect in the clamping levers 16, 18, as a result of which the second, longer lever arms 16", 18" are pressed outwards away from the axis of the tool to be clamped, and the first, shorter lever arms 16', 18' are correspondingly pressed inwards. The normal forces (clamping force) exerted by the clamping levers 16, 18 on the tool are thereby greatly intensified. In order to ensure this leverage effect, the collet is designed such that the second, longer lever arms 16", 18" are not only significantly longer than the first, shorter lever arms 16', 18', but also have a greater mass. The ratio can be in the range of about 4:1.

To prevent the collet 14 from slipping within the housing 12, it is fixedly secured via the engaging pieces 28 to the second guide bushing 26 and thus to the housing 12.

A further embodiment of the invention is shown in a sectional view in FIGS. 5 to 8. In this development on the invention, the clamping force of the clamping device is maintained even after a drop in rotational speed.

As far as the second embodiment corresponds with the first, the same reference numbers are used. Reference is made to the above description of the individual components.

The second embodiment differs from the first in that the engaging piece 32 is formed on the first guide bushing 22 and not on the second guide bushing 26. This means that the required transport of the collet 14 in the rotational direction does not take place, as in the first embodiment, on the clamping side, i.e. not at the clamping diameter D, but rather is transferred to the side of the second, longer lever arms 16", 18". On rotation of the dental turbine, the engaging piece 32 in this second embodiment thus causes an additional spreading apart of the second, longer lever arms 16", 18" and thereby an intensification of the clamping force through inertia at the beginning of the movement. Conversely, in the previously described embodiment, torque applied to the tool via the engaging piece 28 has a negative effect on the clamping force because the frictional forces in the direction of the circumference contribute in opening the collet 14. This contribution, however, is not so large that it jeopardizes the tight fit of the dental tool; since as the rotational speed increases, the clamping force increases in turn in the region of the shorter lever arms due to the contribution of the centrifugal force acting on the longer lever arms, or wings.

In the second embodiment of the invention, the engaging piece 32 is designed such that the two wings, i.e. the second, longer lever arms 16", 18" of the collet 14 are pressed apart when the collet 14 moves out of the first guide bushing 22. To this effect, the engaging piece 32 has a thickened section at its end. In addition, this embodiment has a detent mechanism in order to hold the collet 14 in position in an axial direction when the wings 16", 18" are spread apart. In the illustrated embodiment, the detent mechanism comprises a detent ball 34 that is moveable in a radial direction between a receiving space 36, which is accommodated in the impeller 10, and a bore 38 in the collet 14 through a further bore 40 in the housing 12. The detent ball 34 is preloaded in the receiving space 36 by means of a spring-loaded wedge 42.

In order to clamp a dental tool, the clamping device is brought into the position shown in FIGS. 5 and 6 in that the push button 30 is pressed in the direction of the arrow. The two longer lever arms 16", 18" are thereby pushed into the first guide bushing 22 and pressed together by its wedge-shaped inner surface, so that the opposing shorter lever arms 16', 18' move apart. This causes the clamping diameter D to widen and a dental tool can be inserted into or removed from the clamping device. The ends of the longer lever arms 16", 18" are formed such that they engage around the thickened section of the engaging piece 32 and the two "wings" 16", 18" can be pressed together. The outside surface of the collet 14 blocks the bore 40 in the housing 12, so that the detent ball 34 is pressed into the receiving space 36.

When the push button 30 is released, see FIGS. 7 and 8, the two longer lever arms 16", 18" are released and, due purely to their elasticity, press the collet 14 out of the first guide bushing 22. This displacement of the collet 14 out of the guide bushing 22 is aided when the dental turbine rotates at no-load speed. Due to centrifugal forces, the rotation causes an elastic deformation of the wings 16", 18" towards the outside. Through being guided along the wedge-shaped inner surface of the guide bushing 22, the spreading movement of the wings 16", 18" is transformed into a translational movement, so that the collet 14 is displaced in an axial direction with respect to the housing 12, as indicated by the arrows in FIG. 7. Owing to the shape of the guide bushing 22 and its engaging piece 32 with even parallel surfaces 27 forming a locking mechanism, the two wings 16", 18" are held in their spread-out state. Slight movements are inhibited by the shape of the engaging piece. In addition, the detent ball 34 locks the collet 14 in this position, the engagement of the detent ball 34 being ensured by the spring-loaded wedge 42. Thus, in this embodiment, should there be a drop in rotational speed, not only is the centrifugal force resulting from the momentary rotational speed utilized, but also the spreading of the wings 16", 18" at no-load speed, i.e. at the highest occurring centrifugal force, is in effect "stored". To loosen the collet 14, the detent mechanism and the elastic deformation of the collet have to be overcome in that the push button 30 is pressed inwards as shown in FIGS. 5 and 6.

FIGS. 9 to 13 show a further embodiment of the clamping device according to the invention. The principle behind the clamping device is basically the same as in the previous embodiments. Corresponding parts are indicated by the same reference numbers. This third embodiment differs from the previous embodiments through the spatial arrangement of the collet 14. In contrast to the previous embodiments, in the embodiment of FIGS. 9 to 13, the two longer lever arms 16", 18" of the collet extend in the direction of the push button 30, whereas the two shorter lever arms 16', 18' interact with the first guide bushing 22 and face away from the push button 30. In the third embodiment, the clamping device comprises, just as in the previous embodiments, a housing 12 and a collet 14, having a first and a second clamping lever 16, 18. The collet 14 is fixed and operated in the housing via a first guide bushing 22 and a second guide bushing 26. The first guide bushing 22 has an engaging piece 32, and the second guide bushing 26 has a spreading element 28. The collet 14 is operated using a push button 30 and an intermediary spring assembly 44 that forms a return mechanism as described in more detail below.

In this third embodiment, the collet 14 is fixedly held in the housing 12 in an axial direction in a form fit and secured for the transmission of torque by the engaging piece 32 on the first guide bushing 22.

FIGS. 10 and 11 illustrate the opening mechanism of the clamping device, i.e. the opened clamping device for the insertion of a tool. In this embodiment, the second guide bushing 26 is supported in a housing 12 and is moveable in an axial direction. The guide bushing 26 is designed such that it presses the second, longer lever arm 16", 18" of the clamping lever 16, 18 in the direction of the axis of the tool to be clamped when the guide bushing 26 is pushed in the direction of the collet 14. This causes the first, shorter lever arm 16', 18' to move away from the axis of the tool to be clamped, making the tool easier to loosen. For this purpose, the displaceable second guide bushing 26 has a wedge-shaped inner surface along which the second lever arm 16", 18" of the clamping lever 16, 18 slides, so that on entry into the guide bushing 26 it is pressed in the direction of the axis of the tool shank to be clamped and when going out from the guide bushing can move away from the axis of the tool shank.

In this embodiment of the invention, which can be combined with the above-mentioned features, a push-button mechanism is provided that acts in an axial direction on the second guide bushing 26 in order to displace the latter in an axial direction. The clamping lever 16, 18 can thereby be pressed, for example, into the guide bushing 26 in order to press the second lever arm 16", 18" in the direction of the axis of the tool to be clamped and thus to reduce the clamping force of the first lever arm 16', 18' when a tool change is to be made. On release of the push button, the clamping lever 16, 18 slides out of the guide bushing 26. In addition, due to centrifugal forces during rotation of the clamping device, the second lever arm 16", 18" is pressed away from the axis of the tool to be clamped. The axial displacement of the second guide bushing 26 can be aided by a return mechanism, such as by a spring assembly 44, or, with an appropriate design of the guide bushing 26, also effected by the influence of the centrifugal force.

FIGS. 12 and 13 show the clamping device of the third embodiment in a position for clamping a tool. For this purpose, in this further embodiment of the invention, a spreading element 28 is provided in the region of the second lever arm 16", 18", for example, at the second guide bushing 26, the clamping lever 16, 18 coming to lie against this spreading element 28 when the second guide bushing 26 slides out of the collet 14. The spreading element 28 exerts a force acting outwards in a radial direction or in the direction of the circumference on the second lever arm 16", 18", in order to spread the latter away from the axis of the tool shank to be clamped and thus to maintain via even surfaces 27 the clamping force of the first lever arm 16, 18. Through the additional spring assembly 44, this effect can be created without a centrifugal force effect, so as to increase the clamping force when at a standstill.

Under the effect of the centrifugal force, the second, longer lever arms 16", 18" can be spread further away from the axis of the tool shank to be clamped. The return mechanism, for example, the spring assembly 44, forces the second guide bushing 26 to be removed further away from the collet 14. The spreading element 28 is thereby moved further into the profile now made free by the longer lever arms 16", 18" of the collet 14. The spreading element 28 is designed such that at the end of the movement, the longer lever arms 16", 18" come to rest on an even surface parallel to the axis of the tool shank to be clamped. In addition, the spreading element 28 has a larger section at its end than the clamping lever 16, 18 is able to make free due to the effect of the centrifugal force. In this way, the second guide bushing 26 with the push button 30 and return mechanism (spring assembly 44) is held in the housing 12.

FIGS. 14 and 15 show an exploded view and a sectional view of a modification of the embodiment of the clamping device 50 according to the invention described with reference to FIGS. 9 to 13. Identical components are indicated by the same reference numbers and are not described again in detail. The modification illustrated in FIGS. 14 to 15 is largely identical to the embodiment of FIGS. 9 to 13, reference being made to their description. It only differs in the design of the first guide bushing 22' and the engaging piece 32' formed thereon, as well as in the design of the push button 30' and the associated return spring 44'. As shown in FIGS. 14 and 15, the push button 30' engages in a cylindrical spring 44' and, using the restoring force of the spring, can operate the second guide bushing 26, in order to spread the longer lever arms of the collet 14 and thus press together the shorter lever arms in order to clamp a tool.

The modification shown in FIGS. 14 and 15 further differs in the design of the engaging piece 32' on the first guide bushing 22'. The engaging piece 32' is given the form of a simple projection that engages in a corresponding groove 46' at the end of the shorter lever arm of the collet 14. For further details about the collet and the operation of the collet, reference is made to the above description of FIGS. 9 to 13.

The features revealed in the above description, the claims and the figures can be important for the realization of the invention in its various embodiments both individually and in any combination whatsoever.

IDENTIFICATION REFERENCE LIST

10 Impeller
12 Housing
14 Collet
16 Clamping lever
18 Clamping lever
16', 18' First, shorter lever arm
16", 18" Second, longer lever arm
20 Fulcrum or rotational axis
22, 22' First guide bushing
24 Return spring
26 Second guide bushing
28 Engaging piece, spreading element
30, 30' Push button
32, 32' Engaging piece, spreading element
34 Detent ball
36 Receiving space
38 Bore in collet
40 Bore in housing
42 Spring-loaded wedge
44, 44' Spring assembly
46' Groove
A Axis of the tool shank to be clamped
D Clamping diameter

The invention claimed is:

1. A clamping device for a dental tool in a dental turbine handpiece having at least one clamping lever that can be deflected about a virtual fulcrum and that extends along a longitudinal axis of a tool shank to be clamped,
   wherein the at least one clamping lever is designed and arranged such that the tool shank can be clamped using the at least one clamping lever and that on rotation of the clamping device about the longitudinal axis, through the effect of a centrifugal force, the at least one clamping lever is radially deflected about the virtual fulcrum so as to increase the clamping force acting on the tool shank, and
   wherein the at least one clamping lever forms part of a collet that has a plurality of clamping levers disposed about the longitudinal axis of the tool shank to be clamped;
   a spreading element for maintaining the clamping force of the at least one clamping lever even when the centrifugal force is decreased;
   a push button for applying an external force to the collet; and
   a housing in which the collet is supported so as to translate in an axial direction when subject to the external force.

2. A clamping device according to claim 1, further comprising a locking device that releasably locks the at least one clamping lever in an axial direction.

3. A clamping device according to claim 2, wherein the locking device has a detent mechanism that locks the clamping levers in a predetermined position with respect to the housing.

4. A clamping device according to claim 1, further comprising a locking device; wherein the locking device has a detent mechanism that locks the at least one clamping lever in a predetermined position with respect to the housing.

5. A clamping device according to claim 1, wherein the at least one clamping lever is designed as a two-armed clamping lever having a first and a second lever arm deflectable about the virtual fulcrum, the clamping device further comprising a guide bushing, wherein the at least one clamping lever can be inserted with the second lever arm into the guide bushing in an axial direction, so as to press the second lever arm inwards toward the longitudinal axis of the tool shank to be clamped.

6. A clamping device for a dental tool in a dental turbine handpiece having at least one clamping lever that can be deflected about a virtual fulcrum and that extends along a longitudinal axis of a tool shank to be clamped,
   wherein the at least one clamping lever is designed and arranged such that the tool shank can be clamped using the at least one clamping lever and that on rotation of the clamping device about the longitudinal axis, through the effect of a centrifugal force, the at least one clamping lever is radially deflected about the virtual fulcrum so as to increase the clamping force acting on the tool shank,
   wherein the at least one clamping lever forms part of a collet and the at least one clamping lever is designed as a two-armed clamping lever having a first and a second lever arm deflectable about the virtual fulcrum,
   wherein the tool shank can be clamped using the first lever arm, and
   wherein the first and the second lever arms are configured such that on rotation of the clamping device, the second lever arm, through the effect of the centrifugal force, is deflected about the virtual fulcrum, so as to increase the clamping force of the first lever arm;
   a spreading element for maintaining the clamping force of the at least one clamping lever even when the centrifugal force is decreased; and
   a guide bushing, wherein the at least one clamping lever can be inserted with the second lever arm into the guide bushing in an axial direction upon axial translation of said collet, so as to press the second lever arm inwards toward the longitudinal axis of the tool shank to be clamped.

7. A clamping device according to claim 6, wherein the mass of the second lever arm is greater than the mass of the first lever arm.

8. A clamping device according to claim 6, wherein the guide bushing is fixed in a housing.

9. A clamping device according to claim 6, wherein the guide bushing has a wedge-shaped inner surface.

10. A clamping device according to claim 6, wherein the spreading element comes to lie between a first portion and a second portion of the second lever arm and presses apart the first and second portions of the second lever arm.

11. A clamping device for a dental tool in a dental turbine handpiece having at least one clamping lever that can be deflected about a virtual fulcrum and that extends along a longitudinal axis of a tool shank to be clamped,
  wherein the at least one clamping lever is designed and arranged such that the tool shank can be clamped using the at least one clamping lever and that on rotation of the clamping device about the longitudinal axis, through the effect of a centrifugal force, the at least one clamping lever is radially deflected about the virtual fulcrum so as to increase the clamping force acting on the tool shank,
  wherein the at least one clamping lever forms part of a collet and the at least one clamping lever is designed as a two-armed clamping lever having a first and a second lever arm deflectable about the virtual fulcrum,
  wherein the tool shank can be clamped using the first lever arm, and
  wherein the first and the second lever arms are configured such that on rotation of the clamping device, the second lever arm, through the effect of the centrifugal force, is deflected about the virtual fulcrum, so as to increase the clamping force of the first lever arm; and
  a spreading element for maintaining the clamping force of the at least one clamping lever even when the centrifugal force is decreased,
  wherein the at least one clamping lever comes to rest against said spreading element on axial translation of said collet and which exerts a force acting outwards in a radial direction on the second lever arm.

12. A clamping device according to claim 11, wherein the spreading element comes to lie between a first portion and a second portion of the second lever arm and presses apart the first and second portions of the second lever arm.

* * * * *